(12) United States Patent
Click

(10) Patent No.: US 8,414,886 B2
(45) Date of Patent: Apr. 9, 2013

(54) METHOD OF TREATING DISEASE

(75) Inventor: Robert E. Click, River Falls, WI (US)

(73) Assignee: ParaLab LLC, River Falls, WI (US)

( * ) Notice: Subject to any disclaimer, the term of this patent is extended or adjusted under 35 U.S.C. 154(b) by 70 days.

(21) Appl. No.: 12/718,100

(22) Filed: Mar. 5, 2010

(65) Prior Publication Data

US 2010/0221227 A1 Sep. 2, 2010

Related U.S. Application Data

(62) Division of application No. 10/516,640, filed as application No. PCT/US03/17540 on Jun. 3, 2003, now Pat. No. 8,231, 867.

(60) Provisional application No. 60/385,232, filed on Jun. 3, 2002.

(51) Int. Cl.
*A01N 63/00* (2006.01)
*A61K 39/02* (2006.01)
*A61K 35/00* (2006.01)
*A61K 39/00* (2006.01)

(52) U.S. Cl. .................. 424/93.4; 424/93.1; 424/234.1; 424/282.1; 424/184.1

(58) Field of Classification Search .................. 424/93.4
See application file for complete search history.

(56) References Cited

U.S. PATENT DOCUMENTS 5,989,892 A 11/1999 Nishimaki et al.
6,139,844 A 10/2000 Alkemade et al.
6,156,322 A 12/2000 Hermon-Taylor et al.
8,231,867 B2 7/2012 Click

FOREIGN PATENT DOCUMENTS

WO 99/05304 2/1999
WO 99/49054 9/1999

OTHER PUBLICATIONS

Derwent, Abstract for JP 2001-342147, 2002, Derwent, Acc. No. 2002-247253, pp. 1-4.*
Rainey, et al., 1995, International Journal of Systematic Bacteriology, 45, 32-36.*
Mishra et al., 2011, Molecular Microbiology, 80, 1241-1259.*
Kruis W., "Review article: antibiotics and probiotics in inflammatory bowel disease," 2004, Ailment. Pharmacol. Ther., 20, 75-78.
Duckworth, A.W., et al., "*Dietzia natronolimnalos* Sp. Nov., A New Member of the Genus Dietzia Isolated from an East African Soda Lake," Extremophiles, Springer-Verlag, Tokyo, JP, vol. 2, No. 3, Aug. 1998, pp. 359-366.
Database WPI Section CH, Week 200013, Derwent Publications Ltd., Londong, GB; AN 2000-145986 XP002388668 & RU 2 120 992 CI (Markov I I), Oct. 27, 1998.

* cited by examiner

*Primary Examiner* — Ruth Davis
*Assistant Examiner* — Sheridan Macauley
(74) *Attorney, Agent, or Firm* — Michael Best & Friedrich LLP

(57) ABSTRACT

This invention relates to compositions comprising a bacterium of the genus *Dietzia* that is useful for treating paratuberculosis in ruminants and to a method for culturing the bacterium. The invention further relates to methods of treating Johne's disease by administering to a mammal a composition of the invention.

21 Claims, No Drawings

METHOD OF TREATING DISEASE

STATEMENT OF RELATED REFERENCES

This application is a divisional application of, and claims priority under 35 U.S.C. §§121 and 365(c) to, U.S. patent application Ser. No. 10/516,640, now U.S. Pat. No. 8,231,867 which claims priority to international patent application PCT/US03/17540 filed Jun. 3, 2003, which claims priority to U.S. Provisional Application No. 60/385,232, filed Jun. 3, 2002, the entire disclosures of which are incorporated herein by reference.

TECHNICAL FIELD

The present invention relates to a novel bacterium and the use of the novel bacterium and other members of its genus, active portions thereof and/or proteins therefrom to treat a variety of diseases. More specifically, the invention relates to the use of a bacterium species within the genus *Dietzia*, including the bacterium *Dietzia* sp. C79793-74, and other bacteria isolated by an in vitro inhibition procedure used to isolate *Dietzia,* portions and/or proteins produced therefrom, to treat paratuberculosis of ruminants and mycobacterial-caused diseases of humans, such as Crohn's disease, leprosy, Sarcoidosis, and tuberculosis (ICE).

BACKGROUND OF THE INVENTION

Paratuberculosis, or Johne's disease, in ruminants is a chronic infection of the gastrointestinal tract. *Mycobacterium paratuberculosis* (MpT) is known to be the causative agent of Johne's disease. Most animals that contract Johne's disease become infected shortly after birth and do not become clinically ill until they are adults. Infection is permanent, there are no viable treatments, and, if not culled, most clinically sick animals eventually die of wasting.

Current estimates indicate that 3.4% of dairy cows in 21.6% of herds and 0.9% of beef cattle in 7.9% of herds in the United States are infected with MpT. Similar data are reported in essentially all other countries. These results demonstrate that Johne's disease is a very serious worldwide problem. Indeed, it has been estimated to have a $0.2-1.5 billion dollar economic impact in the United States due to loss of milk income, increased culling, low culling weights, extended calving intervals, and the unmarketability of breeding stock. Similarly, large economic losses from Johne's disease are also suffered in the sheep industry.

It is generally accepted that for clinical manifestation of paratuberculosis to occur, infection with MpT must occur at a young age. To date, no effective treatment has been reported for infected animals. Moreover, no prophylaxis has been reported that prevents infection. Biosecurity and other management practices have been proposed as a means to control the spread of Johne's disease. It is agreed that the spread of MpT could be lessened by: a) persistent attention to detail; b) avoidance of contact with fecal material from infected animals; and c) culling all infected and all offspring born to infected cattle. However, from a practical perspective, it has been suggested that management alone will likely fail to control infections. Thus, there is a need for viable methods to prevent and control paratuberculosis.

*Mycobacteria* are major pathogens of humans, as well as animals. There are approximately ten million cases of tuberculosis worldwide with an annual mortality of three million. Leprosy, caused by *Mycobacterium leprae,* afflicts over ten million people, primarily in developing countries. *Mycobacterium tuberculosis* and mycobacteria of the *Mycobacterium avium*-intracellulare group are major opportunistic pathogens of immuno-compromised patients such as AIDS patients. Crohn's disease and Sarcoidosis are postulated to be a result of MpT infection. Most treatments for these diseases require intense and lengthy combinational drug therapy. Such treatments not only allow resistant strains to arise, but for Crohn's patients lasting resolution of disease has yet to be established. Thus, there is a need for more effective treatments for mycobacterial-incited diseases of humans.

Crohn's disease is a chronic, debilitating and potentially fatal disease that bears extensive clinical, pathologic, and systemic similarity to Johne's disease. In the United States, the number of newly diagnosed Crohn's patients is estimated to be 20,000 each year. Crohn's disease is a granulomatous ileo-colitis of unknown etiology. Postulates on the immunopathogenesis of Crohn's disease are that the disease results from an antigenic challenge to the gut-associated lymphoid tissues (GALT). Once triggered, cytokines and other inflammatory mediators released result in chronic and persistent inflammation. This inflammatory reaction is postulated to be the result of hyper-responsiveness of GALT to antigens present within intestinal cells. This hyper-reactivity may be a result of an immunoregulatory defect or from a persistent stimulus, such as MpT antigens. Recent evidence defining a genetic predisposition is consistent with this theory. Thus, there is a need for treatments for Crohn's disease that target MpT in particular.

Animals afflicted with Johne's disease may be the source of MpT that underlie Crohn's disease in humans. For example, MpT may be transmitted to humans through contaminated meat and/or pasteurized milk. MpT is an intracellular pathogen that colonizes and multiplies in phagocytic cells present in blood and other tissues. Since phagocytes are natural constituents of milk, it is not surprising that MpT is found in milk of infected cows. Moreover, MpT is partially resistant to pasteurization presently used commercially. Furthermore, animals that are heavily infected with MpT are usually culled and likely used in the production of ground beef. Inadequate cooking would again result in live MpT being present in food. Thus, any effective treatment of paratuberculosis is likely to reduce the transmission of MpT to humans, which could in turn result in a lower incidence of Crohn's disease.

SUMMARY OF THE INVENTION

The present invention relates to the use of bacteria of the genus *Dietzia* for the treatment of various diseases. The invention includes the use of an isolated bacterium identified as *Dietzia* sp. C79793-74 and deposited with the American Type Culture Collection (ATCC), located at 10801 University Blvd, Manassas, Va. 20110-2209 USA, as Accession Number PTA-4125 on Mar. 7, 2002, for the treatment of various diseases.

In one embodiment, the invention includes a composition suitable for administration to an animal comprising a carrier and one or more bacteria, the bacteria species selected from the genus *Dietzia,* including ATCC Accession Number PTA4125, referred to collectively herein as "The Bacteria".

The invention further includes a composition suitable for administration to an animal comprising a carrier and a pharmacologically active, or recombinant DNA-derived, dose of The Bacteria, active fragments of The Bacteria, including active fragments of enzymes, active molecules secreted from The Bacteria or from organisms with The Bacteria-derived DNA, and combinations of the above. Active molecules include proteins, DNA molecules, RNA molecules, carbohydrates, and components of the cell envelope, such as lipoglycans.

In another embodiment, the invention includes compositions that are suitable for administering The Bacteria to animals affected by Johne's disease. For example, the invention encompasses feed compositions and feed additives in which The Bacteria is an ingredient.

In still another embodiment, the invention includes a composition suitable for administration to a human comprising a suitable carrier and The Bacteria.

The invention further includes a composition suitable for administration to a human comprising a carrier and a pharmacologically active, or recombinant DNA-derived, dose of The Bacteria, active fragments of The Bacteria, active molecules secreted from The Bacteria or from organisms with The Bacteria-derived DNA, and combinations of the above. Methods for producing bacteria through recombinant processes are well known in the art.

In addition, the invention relates to methods of treating Johne's disease, Crohn's disease, and other mycobacterial-caused diseases by administering a composition comprising The Bacteria. In one embodiment, the invention includes a method of treating Johne's disease comprising orally administering a composition comprising The Bacteria to any mammals infected with MpT.

The bacteria used in the present invention are isolated from an animal sample, which may be the feces of bovine, co-culturing the bacterium with MpT, and selecting bacteria that inhibit the growth of MpT. In other embodiments, the bacterium are (or bacteria is) isolated from soil, sea water, or even insects.

The method also relates to a method of culturing bacteria of the genus *Dietzia* in a medium containing Tryptose soy broth.

DETAILED DESCRIPTION OF THE INVENTION

All ranges recited herein include all combinations and sub-combinations included within that range; therefore, a range from "about 15 to about 60" would include ranges from about 15 to about 45, from about 30 to about 47, etc. A range of "up to 85" would include up to 80, up to 50, up to 24, etc.

The present invention relates to novel bacteria such as those species within the *Dietzia* genus ("The Bacteria"), that, when co-cultured with a pathogenic mycobacterium, inhibit the growth of the co-cultured mycobacterium and therefore prove useful in controlling the growth of said mycobacterium.

The Bacteria have also surprisingly and unexpectedly proved to be effective in treating MpT infected cattle, including those with and those without clinical disease.

Specifically, administering The Bacteria to ruminants has solved a longstanding problem in that it has proved to be effective for treating MpT-infected ruminants. It has been surprisingly and unexpectedly discovered that the oral administration of The Bacteria in a pharmacologically active dose to cattle treats the symptoms of Johne's disease and results in long term health benefits to the administered ruminant.

The bacterium is effective to treat Johne's disease in any ruminant, including, but not limited to, bovine, ovine, caprine, and cervine. Administration of The Bacteria to clinically, asymptomatic MpT-infected ruminants is also useful in preventing the onset of clinical symptoms of Johne's disease. In one embodiment, the ruminants include bovines, such as dairy calves and adult lactating and nonlactating cows. In another embodiment, the ruminants include caprine or ovine.

The Bacteria in one embodiment is administered to the ruminant orally. The Bacteria may be administered in a solution, mixed with a feed and/or mixed with a feed additive. The oral administration may be given in a series of doses administered daily for a period of at least 3 months. When the ruminant is a bovine, the treatment may be administered for at least 6 months at a dosage of at least 10.sup.11 cfu. This includes methods of treatment where The Bacteria is administered at a dosage of at least 10.sup.12 cfu and further includes methods of treatment where The Bacteria is administered at a dosage of at least 10.sup.13 cfu. In one embodiment, The Bacteria are administered orally to adult clinically-ill or asymptomatic dairy cows on a daily basis for about 3-10 months. However, any acceptable time period may be used as long as a pharmacologically effective dose is administered such that paratuberculosis is effectively prevented and/or cured. For example, if The Bacteria is mixed with a feed and/or feed additive, ruminants may be fed on a constant diet of feed containing a pharmacologically effective dose of The Bacteria until a total pharmacological dose results in cure and/or prevention of disease.

In one embodiment, 2.times.10.sup.11 cfu of The Bacteria are administered daily, in a single dose. If The Bacteria are incorporated into feed, a range of concentrations of The Bacteria in the feed are appropriate to practice the method of the invention, in one embodiment about 10.sup.11-10.sup.13 cfu per day. In one embodiment, The Bacteria are incorporated into the feed at a concentration such that 2.times.10.sup.11 cfu of The Bacteria are administered in an amount of feed that is consumed in a single day. Any appropriate amount of The Bacteria, or active portions or proteins thereof, may be incorporated into the feed as long as a pharmacologically active dose of the material is fed to the animal within a daily feed. If The Bacteria are incorporated into a feed additive, a range of concentrations of The Bacteria in the feed additive are appropriate to practice the method of the invention, in one embodiment about 10.sup.11 cfu per day. In one embodiment, The Bacteria are incorporated into the feed additive at a concentration such that 2.times.10.sup.11 cfu of The Bacteria are administered in an amount of feed that is consumed in a single day.

It is not intended that the present invention be limited by the particular nature of the therapeutic preparation. The Bacteria can be prepared in any type of appropriate medium for administration. For example, The Bacteria can be provided together with physiologically tolerable liquid (e.g., saline), gel or solid carriers, diluents, adjuvant, excipients and as a rumen-protected encapsulated ingredient. Suitable diluents and excipients include pharmaceutical grades of physiological saline, dextrose, glycerol, mannitol, lactose, starch, magnesium stearate, sodium saccharin, cellulose, magnesium carbonate, and the like, and combinations thereof. In addition, if desired the compositions may contain minor amounts of auxiliary substances such as wetting or emulsifying agents, stabilizing or pH buffering agents. These compositions typically contain 1%-95% of active ingredient, preferably 2%-70%. The Bacteria can be incorporated into tablets, boluses, or capsules, and dosed to the patient. The Bacteria may also be incorporated into salt blocks and the like. The Bacteria can be added to feed as a freeze-dried powder or as an encapsulated bacteria that is protected from degradation in the rumen. In one embodiment, The Bacteria is prepared in a solution of physiological phosphate-buffered saline (PBS) or in the culture medium, Tryptose soybean broth (TSB) for oral administration to a ruminant.

The Bacteria can be incorporated into tablets, drenches, boluses, capsules or premixes. Formulation of these active ingredients into such dosage forms can be accomplished by means of methods well known in the pharmaceutical formulation arts. See, for example, U.S. Pat. No. 4,394,377. (This patent, and all other references cited herein are hereby incorporated by reference.) Filling gelatin capsules with any desired form of the active ingredients readily produces capsules. If desired these materials can be diluted with an inert powdered diluent, such as sugar, starch, powdered milk, purified crystalline cellulose, or the like to increase the volume for convenience of filling capsules.

Conventional formulation processes can be used to prepare tablets containing The Bacteria. In addition to the active ingredients, tablets may contain a base, a disintegrator, an absorbent, a binder, and a lubricant. Typical bases include lactose, sugar, sodium chloride, starch and mannitol. Starch is also a good disintegrator as is alginic acid. Surface-active agents such as sodium lauryl sulfate and dioctyl sodium sulphosuccinate are also sometimes used. Commonly used absorbents include starch and lactose. Magnesium carbonate is also useful for oily substances. As a binder there may be used, for example, gelatin, gums, starch, dextrin, polyvinyl pyrrolidone and various cellulose derivatives. Among the commonly used lubricants are magnesium stearate, talc, paraffin wax, various metallic soaps, and polyethylene glycol.

Drenches are prepared most readily by choosing a saline-suspended form of The Bacteria, fragments thereof or active molecules secreted therefrom. A water-soluble form of one ingredient may be used in conjunction with a water-insoluble form of the other by preparing a suspension of one with an aqueous solution of the other. Water-insoluble forms of either active ingredient may be prepared as a suspension or in some physiologically acceptable solvent such as polyethylene glycol. Suspensions of water-insoluble forms of either active ingredient can be prepared in oils such as peanut, corn, sesame oil or the like; in a glycol such as propylene glycol or a polyethylene glycol; or in water depending on the solubility of a particular active ingredient. Suitable physiologically acceptable adjuvants may be necessary in order to keep the active ingredients suspended. The adjuvants can be chosen from among the thickeners, such as carboxymethylcellulose, polyvinyl pyrrolidone, gelatin and the alginates. Surfactants generally will serve to suspend the active ingredients, particularly the fat-soluble propionate-enhancing compounds. Most useful for making suspensions in liquid nonsolvents are alkylphenol polyethylene oxide adducts, naphthalenesulfonates, alkylbenzene-sulfonates, and the polyoxyethylene sorbitan esters. In addition many substances, which affect the hydrophilicity, density and surface tension of the liquid, can assist in making suspensions in individual cases. For example, silicone anti-foams, glycols, sorbitol, and sugars can be useful suspending agents.

Additionally the subject compositions of this invention may be separately administered, for example, by adding one directly to feed stuffs and co-administering the second material as a bolus tablet, drench, or capsule. Or each may be separately prepared and separately added to feed stuffs in appropriate quantities and at appropriate times. For example, such a material as choline stearate, a fatty acid complex which may be used in the practice of this invention, may not be appropriate for incorporation into feed premixes because of its physical characteristics. In such an instance the choline stearate composition could be provided separately in a suitable diluent such as, for example, corn flour, ground corn cob, hominy, corn glutenmeal, wheat middlings, soybean meal, soybean mill feed, rice mill by-product, and the like and mixtures thereof. A description of such suitable diluents may be found in U.S. Pat. No. 4,394,377.

The Bacteria may be administered to an animal in a composition, a premix, that is then mixed into the animal feed supply. Such a composition may comprise The Bacteria alone or The Bacteria may be mixed with a carrier and/or with other drugs, vitamins, minerals, protein concentrates and similar feed supplements. These compositions may be prepared in dry granular powder form, as pellets, in the form of pastes, encapsulated to be rumen protected, or may be formulated as liquid feed supplements and the like. Any type of feed may be medicated with such compositions, including common dry feed, liquid feeds, and pelleted feeds. The methods of formulating supplemental materials into animal feeds are well known. It is necessary only to calculate the amount of each compound, which it is desired to administer to each animal, to take into account the amount of feed per day that the animal eats and then mix in the appropriate amount of The Bacteria. See U.S. Pat. No. 4,394,377.

The compositions of the invention may be used as a feed additive premix, feed additive concentrate or feed additive supplement in which the active ingredients are distributed uniformly throughout a standard organic or inorganic animal feed carrier in a concentrated form which is conveniently packaged and shipped to the feed mixer. The grower or the feed mixer then in turn mixes this premix, concentrate or supplement uniformly with a normal diet for the animal as desired. Examples of carriers for premix compositions are soybean meal, corn oil, ground corn, barley, wheat, mineral mixtures containing, e.g., vermiculite or diatomaceous earth, corn gluten meal, soy flour or other modestly priced edible ingredients.

The Bacteria may also be admixed with a suitable carrier such as an edible feed or feed component in the form of a feed additive supplement. Examples of such edible feed components are feed fortifiers and enhancers for preruminant bovine calves of any of the kinds disclosed in U.S. Pat. No. 6,156,333. If to be fed free choice or as a supplement, The Bacteria is provided according to the anticipated daily consumption of the supplement to provide a daily dose of each of these ingredients in one of the ranges specified.

In addition, The Bacteria may be incorporated directly into feeds by a mill or other feed supplier to provide a finished feed product to the grower. A finished feed product could be made up of any of the various grains, lucerne, grasses, minerals, vitamins, protein supplements, drugs and the like which go into the formulation of a nutritionally complete ruminant feed. The Bacteria may be mixed directly with cattle feed made up of various components such as hay, straw, silage, cornstalks, cottonseed hulls, grain, oats, barley and cereal brans, particularly for the ruminants; antioxidants, minerals, vitamins, anthelmintics, and other appropriate medicaments. See U.S. Pat. No. 4,394,377. Alternatively, The Bacteria may be incorporated into a liquid feed for preruminant bovine calves of any of the kinds disclosed in U.S. Pat. No. 6,156,333.

The Bacteria may be mixed into a suitable animal feed by any method appropriate for mixing a bacterium into animal feed. Examples of such methods include but are not limited to the following: spraying The Bacteria onto dry feed and mechanically mixing The Bacteria into dry or liquid feed; top dress grain or concentrate mix.

The Bacteria of the present invention are also useful in treating medical conditions in humans that result from various mycobacterial infections. These include Crohn's, leprosy, tuberculosis, Sarcoidosis, and diarrhea in immuno-compromised (AIDS) patents. Administration of The Bacteria or active fragments, proteins, secretions, etc. thereof by appropriate means known in the art to a human patient should demonstrate a reduction of the symptoms of the disease or syndrome caused by the mycobacterium.

Dietzia sp. 79793-74, ATCC Accession Number PTA4125 was identified as a unique bacterial contaminant during culturing of feces from MpT sero-positive and negative cows. The bacterial contaminant was subsequently isolated, cultured, and identified as being of the Dietzia genus. On further investigation, Dietzia sp. 79793-74 was found to completely inhibit the growth of MpT when co-cultured with MpT. This method of utilizing a sample isolated from an appropriate animal host may be used to isolate other bacteria, in addition to those of the Dietzia genus, that inhibit the growth of MpT and that are therefore useful for treating diseases caused by MpT.

Other micro-organisms that inhibit the growth of various mycobacteria may be isolated by similar means. Other mycobacteria that may be inhibited include M. tuberculosis, M. leprae, M. avium-intracellulare, M. bovis, M. cheloiei (also known as borstelense and abscessus), M. africanum, M. marinium (also known as balnei and platypoecilus, the causative agent of "swimming pool granuloma"), M. buruli (also known as ulcerans), M. fortuitum (also known as giae, minetti, and ranae), M. haemophilum, M. intracellulare, M. kansasii (also known as luciflavum), M. littorale (also known as xenopi), M. malmoense, M. marianum (also known as scrofulaceum and paraffinicum), M. sinuae, M. szulgai, and M. ulcerans (which is the agent responsible for Buruli ulcer), M. avium (also known as brunense), M. flavascens, M. lepraemurium, and M. nicroti.

Bacteria of the Dietzia genus may be cultured by growing the bacteria on agar slants in Tryptose soy broth at 35.degree. C. Large-scale production of Dietzia genus bacteria is achieved by growth in suspension in large biofermenters. Viability of such bacteria is unchanged by storing at −20.degree. C. In addition, bacteria of the Dietzia genus can be stored as a freeze-dried material at room temperature. Other storage methods that maintain bacterial viability that are known in the art may be used.

Active fragments of bacteria from the Dietzia genus and active molecules isolated from such bacteria may be prepared by any known method for preparing/identifying active fragments of bacteria and proteins secreted from bacteria. Such methods include but are not limited to the following: sonication, osmotic shock, detergent lysis, high pressure, transfer appropriate DNA to other organisms, such as bacteria, plant or animal that is then used as a feed additive as described previously.

The compositions and methods of the invention create several important benefits: an effective treatment for Johne's disease is provided which will increase profitability for farmers; products such as milk and meat will be safer for human consumption by eliminating potential MpT contamination; and a potentially effective non-antibiotic treatment for Crohn's patients as well as other diseases caused by mycobacteria, such as tuberculosis and leprosy. The methodology also teaches a way to identify bacteria that inhibit the growth of various mycobacteria.

Those skilled in the art will recognize, or be able to ascertain using no more than routine experimentation, numerous equivalents to the specific embodiments described herein. Such equivalents are within the scope of this invention.

EXAMPLES

The invention is further described in the following, non-limiting examples.

Example 1

Antibodies in Sera and Colostrum/Milk from Dietzia-Sensitized Cows Cross-React with MpT as Determined in an Enzyme-Linked Immunosorbent Assay (ELISA) Assay Healthy cows that tested negative for MpT infection were injected with the indicated doses of Dietzia sp. C79793-74, Accession No. PTA-4125. The titers of antibodies that are cross-reactive with MpT in milk and sera taken from the injected cows were determined by a standard ELISA assay that those skilled in the art will recognize or be able to ascertain.

TABLE 1

| Cow ID # | Injection Date | Injection Dose | ELISA Date | Milk | Serum |
|---|---|---|---|---|---|
| 51 | None | | Jul. 21, 1994 | − | ND |
| | Feb. 03, 1995 | $2 \times 10^{10}$ IM | Feb. 03, 1995 | ND | − |
| | Feb. 17, 1995 | $6 \times 10^{10}$ IM | Feb. 17, 1995 | ND | ND |
| | Mar. 14, 1995 | $4 \times 10^{9}$ IM | Mar. 14, 1995 | + | 4.6 |
| | Apr. 04, 1995 | $4 \times 10^{9}$ IM | May 09, 1995 | ++ | ND |
| | | | Jul. 28, 1995 | + | ND |
| | | | Mar. 08, 1996 | ND | 3.2 |
| B-5 | None | | Jul. 21, 1994 | − | ND |
| | Feb. 03, 1995 | $2 \times 10^{10}$ IM | Feb. 03, 1995 | ND | − |
| | | | Mar. 14, 1995 | ND | 2.3 |
| | Apr. 04, 1995 | $4 \times 10^{9}$ IM | May 09, 1995 | − | ND |
| | | | Jul. 27, 1995 | + | ND |
| | | | Mar. 08, 1996 | ND | − |
| B-10 | None | | Jul. 21, 1994 | − | ND |
| | | | Feb. 03, 1995 | ND | − |
| | Feb. 17, 1995 | $4 \times 10^{10}$ IM | Mar. 14, 1995 | ND | 2.5 |
| | Mar. 14, 1995 | $4 \times 10^{9}$ IM | May 09, 1995 | − | ND |
| | Apr. 04, 1995 | $4 \times 10^{9}$ IM | Mar. 08, 1996 | ND | 2.1 |

Key:
− means negative;
+ means positive;
ND means not done;
IM means intramuscularly The results in Table 1 show that cows immunized with Dietzia bacteria ATCC Accession No. PTA4125 produce antibodies that cross-react with MpT. Moreover, these antibodies are found in both serum and milk. The results are important because they provide a possible explanation for the mechanism of action of the Dietzia bacteria: phagocytes infected with MpT can more readily take up Dietzia bacteria coated with antibodies that cross-react with MpT. Thus, the cross-reactive antibodies may serve to deliver Dietzia bacteria to cells infected with MpT.

Example 2

Treatment of Cows that are Sero-Positive for Johne's Disease

Cows afflicted with Johne's disease were treated according to the method of the invention by administration of Dietzia bacteria ATCC Accession No. PTA4125. The clinical results with seven such cows are shown in Table 2 below. Each cow was administered a single oral dose of 2.times.10.sup.11 cfu, on a daily basis, in a single dose, of *Dietzia* sp. C79793-74, ATCC Accession No. PTA4125.

TABLE 2

| Cow ID # | Calving Dates | Treatment Length | Treatment Observations |
|---|---|---|---|
| H-83 | Aug. 27, 1997<br>Apr. 20, 1999<br>Jul. 20, 2000<br>Aug. 8, 2001 | 9 months | Began showing clinical symptoms on Jan. 1, 1998. Began daily treatments Feb. 25, 1998. Recovered on Apr. 1, 1998. Had a relapse on Oct. 18, 1998 and recovered by Oct. 23, 1998. Stopped treatment on Nov. 13, 1998. She has not had any further relapses but did have a borderline serum ELISA on Oct. 15, 1999 which returned to negative on Jun. 28, 2000 and Aug. 20, 2001. Fecal samples taken Nov. 29, 1999, Jun. 28, 2000, Jan. 1, 2001 and Aug. 20, 2001 were negative. |
| H-51 | Nov. 5, 1996<br>Jul. 17, 1998 | 3 months | Signs of disease on Aug. 1, 1998. Started treatment on Aug. 31, 1998. Recovered. No further symptoms. |
| H-81 | Aug. 30, 1997<br>Mar. 26, 1999 | 6 months | Broke on May 24, 1998; started treatment on May 25, 1998. Recovered. No further symptoms. |
| H-58 | Nov. 3, 1996 | 10 months | Signs of disease on Jan. 10, 1998. Started treatment on Jan. 25, 1998. Recovered. No further symptoms. |
| H-62 | Oct. 25, 1996<br>Feb. 1, 1998 | 10 months | Signs of disease on Jan. 20, 1998. Started on treatment on Jan. 20, 1998. Recovered. Relapse on Oct. 29, 1998. Recovered. No further symptoms. |
| H-53 | Nov. 3, 1996<br>Sep. 4, 1998 | 5 months | Signs of disease on Apr. 7, 1998; Started treatment same day. Recovered. Moved to maternity pen on Aug. 26, 1998. She quit eating on Sep. 1, 1998, calved with difficulty and died with no clinical signs. |
| H-64 | Oct. 21, 1996<br>Mar. 26, 1998 | 7 months | Minor signs of disease in first lactation. Relapse during 2nd lactation on Apr. 7, 1998. Started treatment on Apr. 7, 1998. Although there were times when she appeared to recover, we were not able to turn her around. She eventually died on Nov. 5, 1998 with severe diarrhea and was quite emaciated. |

The results in Table 2 show that treatment of MpT sero-positive animals with *Dietzia* sp. C79793-74, ATCC Accession No. PTA-4125 is effective (and for H-83, curative). For instance, cow H-83, who was treated with *Dietzia* sp. C79793-74, ATCC Accession No. PTA4125 for 9 months remains in the herd as of May 1, 2002, ELISA negative, culture negative and clinically free, 38 months after treatment was terminated. Results also suggest that the best candidates for treatment are those with early-stage disease. Any results such as those shown in Table 2, or similar thereto depending on the mammal to be treated is said to meet the definition of "reducing or preventing the symptoms of a disease or syndrome" as discussed in this application.

To summarize, a clinical study was undertaken in which adult dairy cattle that displayed symptoms of Johne's disease were administered *Dietzia*. sp. C79793-74, ATCC Accession No. PTA4125. In this study, the bacteria was given daily for 3-10 months. Of seven clinically sick animals treated, six recovered. Moreover, four treated animals that were MpT-sero-positive, but clinically asymptomatic, never developed disease. In contrast, the ten MpT-clinically sick animals that were not treated went on to succumb with overt clinical disease.

Example 3

Safety of BC: Administration of *Dietzia* to Calves and Mice

In addition to the cows that were administered live or killed *Dietzia* sp. C79793-74, ATCC Accession No. PTA-4125, a number of calves and mice were also administered the same live bacteria. Two types of mice were used. Eight immunologically competent, 2-3 month old A/J males and eight females (two of each per cage) were injected IP with $10^8$ cfu live *Dietzia* sp. C79793-74, ATCC Accession No. PTA-4125. They were then monitored for ten months for any signs of disease (weight loss, diarrhea) and reproductive problems. All activities monitored were indistinguishable from those of untreated (control) animals. In addition, $10^8$ cfu live *Dietzia* sp. C79793-74, ATCC Accession No. PTA4125 were injected intraperitoneally (IP) into mouse CB.17 severe-combined-immunodeficient mice (SCID) mice. Just as was found with conventional mice, the injected bacteria manifested no detrimental overt reaction even though these mice, genetically, are immunologically incompetent (they lack functional T and B cells).

Seven bull calves destined to become steers were used to determine the safety of $10^9$ cfu *Dietzia* sp. C79793-74, ATCC Accession No. PTA-4125 given orally, as a single dose, on a daily basis, from birth up to 15 days. Two bull calves served as controls and did not receive any of the bacteria. All animals were castrated and raised for slaughter. During their lives of 15-18 months, no signs of disease or sickness were obvious. They were all similar in weight at slaughter. At approximately four months of age, a sample of blood was taken from all nine calves from which the prepared sera was tested for antibodies to MpT in an ELISA assay. All animals were found to be negative, except one calf that had a positive ELISA reading. This was expected since this calf received colostrum from a *Dietzia* sp. C79793-74 hyper-immunized cow (H-51 in Table 1) possessing antibodies in her milk.

The above results show that live *Dietzia* sp. C79793-74 are not pathogenic when administered orally or injected.

Example 4

Treatment of Clinically Sick and/or Asymptomatic Cows

A large study was initiated in which liquid or freeze-dried *Dietzia* sp. C79793-74 is given to clinically sick and/or asymptomatic cows that are either
  a) Sero-ELISA positive, Sero-AGID negative, fecal negative b) Sero-ELISA positive, Sero-AGID positive, fecal negative c) Sero-ELISA positive, Sero-AGID negative, fecal positive d) Sero-ELISA positive, Sero-AGID positive, fecal positive e) Sero-ELISA negative, Sero-AGID negative, fecal positive.

After 7 months, the preliminary results indicate that the dose of the bacteria necessary to prevent death of Johne's positive cows is dependent upon the body weight of the animal being treated. Holsteins for example that weigh up to 2.times. more than Jerseys, need at least 2.times. higher dose of bacteria.

Animals that were ELISA positive and agar gel immunodiffusion (AGID) positive were more difficult to maintain alive than those that were only ELISA positive. Survival did not appear to depend upon whether an animal shed or did not shed MpT.

Of 19 animals (out of 36) found to be shedding MpT in feces, after 6 weeks of treatment, only one was found to still be shedding. Of 8 animals that calved while on treatment, none had detectable MpT in their colostrums. This is contrary to what is published. These results suggest that is it possible that the treatment prevented shedding in colostrums.

A number of animals (12) died during treatment, most due to complications such as displaced abomasums. Only 4 died due to Johne's and they were all AGID positive when started on treatment.

In tissues of two animals that were euthanized and autopsied, no *Dietzia* were detected.

Weight changes post treatment of two animals that were or became clinically very sick are shown in Table 3 below.

TABLE 3

| Cow # | weights on Sep. 1, 2001 | Oct. 24, 2001 | Dec. 06, 2001 | Jan. 2, 2002 | Feb. 10, 2002 |
|---|---|---|---|---|---|
| G-4 | 945 | 1095 | 1160 | 1190 | 1090 |
| R100 | 1000 | 840 | 940 | 1045 | 1030* |

Weight prior to treatment
*calved

Treatment appears to reduce shedding of MpT in both feces and milk. Very sick animals gain weight. No *Dietzia* was found systemically in autopsied cows.

Example 5

Long Term Treatment of Antibody Positive Cows

Three cows that tested sero-positive for Johne's disease were treated according to the method of the present invention by administration of *Dietzia* bacteria ATCC Accession No. PTA4125. Each cow was administered a single oral dose of 10.sup.12 cfu, on a daily basis of *Dietzia* sp. C79793-74, ATCC Accession No. PTA-4125. The serum antibody titers specific for MpT as determined in an ELISA assay for these three cows was measured periodically during the treatment period. The results of these measurements are presented in Table 4 below. A value of zero indicates that a test serum is void of antibodies for MpT, whereas a value greater than 1 indicates that the sera is from an animal that is/was infected with MpT.

TABLE 4

| Cow # | Antibody Level in Serum On Day Start Date | 18 | 70 | 95 | 147 | 183 | 235 | 273 | 335 | 341 | 400 | 425 | 490 | 525 | 590 |
|---|---|---|---|---|---|---|---|---|---|---|---|---|---|---|---|
| 13 | 2.2 | | 1.7 | | 1.7 | | 1.6 | | | 0 | 1.8 | | 0 | | |
| 198 | 2.6 | | 2.9 | | 2.4 | | 1.8 | | | 0 | 2.0 | | 0 | | 0 |
| 1734 | 2.2 | 1.9 | | 3.1 | | 2.2 | | 1.8 | 2.0 | | | 2.0 | | 0 | |

Cow 13 died from birthing complications and was autopsied. The autopsy showed no signs of Johne's disease and no growth of MpT from the cow s tissue. The immune systems of the cows were healthy following treatment, therefore, the disappearance of antibodies in the sera of the cows suggest that MpT was no longer present in the animals.

What is claimed is:

1. A method of treating a disease or syndrome whose causative agent is a *Mycobacterium* by administering to a mammal infected with the disease or syndrome a composition, comprising a pharmacologically active dose of a live bacterium of the genus *Dietzia*, the dose being orally administered daily for at least three months.

2. The method of claim 1, wherein the mammal is a bovine.

3. The method of claim 1, wherein the mammal is a human.

4. The method of claim 1, wherein the mammal is a dairy calf.

5. The method of claim 1, wherein the mammal is a ruminant.

6. The method of claim 1, wherein the mammal is an ovine.

7. The method of claim 1, wherein the mammal is a caprine.

8. The method of claim 1, wherein the mammal is a corvine.

9. The method of claim 1, wherein the dose comprises at least $10^9$ cfu of the bacterium.

10. The method of claim 1, wherein the bacterium is deposited with the American Type Culture Collection as Accession Number PTA-4125.

11. The method of claim 1, wherein the composition includes an animal feed.

12. The method of claim 1, wherein the composition includes a feed additive.

13. The method of claim 1, wherein the composition is included within a feed composition, the feed composition selected from the group consisting of grain, hay, straw, silage, cornstalks, corn, corn meal, corn glutenmeal, soybean meal, soy flour, soybean mill feed, cottonseed hulls, oats, barley, hominy, cereal brans, rice mill by-product and mixtures thereof.

14. The method of claim 1, wherein the composition is included within a feed additive, the feed additive selected from the group consisting of vitamins, minerals, protein supplements, drugs, and mixtures thereof.

15. The method of claim 1, wherein the composition is incorporated into a dosage form selected from the group consisting of tablets, drenches, boluses, and capsules.

16. The method of claim 1, wherein the composition is incorporated into a tablet.

17. The method of claim 1, wherein the composition is administered to a mammal having Johne's disease.

18. A method of treating a mammal infected with a disease whose causative agent is a *Mycobacterium*, comprising administering to the mammal a pharmacologically active dose of a live bacterium of the genus *Dietzia* on a daily basis.

19. The method of claim 18, wherein the dose is given daily for up to three to ten months.

20. The method of claim 18, wherein the bacterium is *Dietzia* species C79793-74 having an ATCC accession number of PTA-4125.

21. The method of claim 18, wherein the daily dose is from $10^9$ cfu to $10^{13}$ cfu.

* * * * *